United States Patent [19]

Pethö

[11] Patent Number: 5,033,158
[45] Date of Patent: Jul. 23, 1991

[54] APPARATUS FOR WASHING ORIENTED STOPPERS IN A CLOSED ENVIRONMENT

[75] Inventor: Lajos Pethö, Limoges, France
[73] Assignee: KabiVitrum AB, Stockholm, Sweden
[21] Appl. No.: 460,874
[22] PCT Filed: May 23, 1989
[86] PCT No.: PCT/SE89/00287
   § 371 Date: Mar. 30, 1990
   § 102(e) Date: Mar. 30, 1990
[87] PCT Pub. No.: WO89/11923
   PCT Pub. Date: Dec. 14, 1989

[30] Foreign Application Priority Data
   Jun. 2, 1988 [SE] Sweden .................. 8802063

[51] Int. Cl.$^5$ .............................. B08B 3/02
[52] U.S. Cl. ...................... 15/302; 15/309.2;
   134/72; 134/126; 134/128; 134/131; 198/484.1
[58] Field of Search ................ 134/72, 126, 127, 128,
   134/131; 15/302, 306 B, 309.2; 198/484.1,
   803.13

[56] References Cited

U.S. PATENT DOCUMENTS

| | | | |
|---|---|---|---|
| 1,109,517 | 9/1914 | Delgoffe | 198/484.1 X |
| 1,178,166 | 4/1916 | McCoe et al. | 134/126 X |
| 1,212,171 | 1/1917 | Beardsley | 134/131 X |
| 1,655,941 | 1/1928 | Dawson et al. | 134/128 X |
| 2,352,709 | 7/1944 | Haase | 134/126 X |
| 4,125,120 | 11/1978 | Standley | 134/126 |
| 4,165,756 | 8/1979 | Sirch et al. | 134/126 X |

FOREIGN PATENT DOCUMENTS

| | | | |
|---|---|---|---|
| 1401408 | 4/1965 | France | 134/72 |
| 0048512 | 3/1982 | Japan | 198/803.13 |
| 127492 | 10/1928 | Switzerland | 134/72 |

Primary Examiner—Philip R. Coe
Attorney, Agent, or Firm—Pollock, Vande Sande & Priddy

[57] ABSTRACT

An apparatus for washing position oriented stoppers in a closed environment while retaining the orientation comprises a closed chamber, and a chain conveyor located in the closed chamber for receiving position oriented stoppers. The chain conveyor includes two spaced chain wheels, and a chain passing over the chain wheels. A plurality of dogs are fixedly attached to at least some of the chain links. The chain conveyor defines curved portions around the chain wheels and straight portions therebetween. A supply conveyor communicates with the closed chamber at a location of one of the chain wheels. A washing station is located along one of the straight portions and a closed delivery member is in communication with a closed chamber at the other chain wheel. The dogs grip each stopper between two adjacent dogs and carry them along the straight portions of the conveyor. The dogs move away from each other while passing together with the chain links along the curved portions to allow receiving the stoppers from the supply conveyor, carrying the position oriented stoppers along the straight portion past the washing station and releasing and feeding the stoppers in the retain orientation to the delivery member.

5 Claims, 2 Drawing Sheets

APPARATUS FOR WASHING ORIENTED STOPPERS IN A CLOSED ENVIRONMENT

FIELD OF THE INVENTION

The present invention relates to an apparatus for washing already oriented stoppers in a closed environment while retaining the orientation of the stoppers. Such an apparatus is used, for example, in the medicament industry for disinfecting or sterilizing stoppers which are to be used for closing medicament bottles and the like, and where it is important that the stoppers are clean so that they do not contaminate the medicament.

The apparatus in accordance with the invention is used as a step in conveying the stoppers, for example, to the station where they are to be put into the container which is to be closed, or to a sterilizer, and the apparatus is arranged after a plant for orienting the stoppers and after an apparatus for their quality and dimensional control.

SUMMARY OF THE INVENTION

The object of the present invention is to provide an apparatus of the kind mentioned above, which guarantees reliable washing in a closed environment, and at the same time an apparatus which requires a minimum of space in the place where work is carried out and which does not prevent normal paths of communication.

BRIEF DESCRIPTION OF THE DRAWINGS

The present invention will now be described in the form of an unrestricting embodiment example, illustrated on the accompanying drawing figures, where.

DETAILED DESCRIPTION OF THE PREFERRED EMBODIMENT(S)

Figure 1:
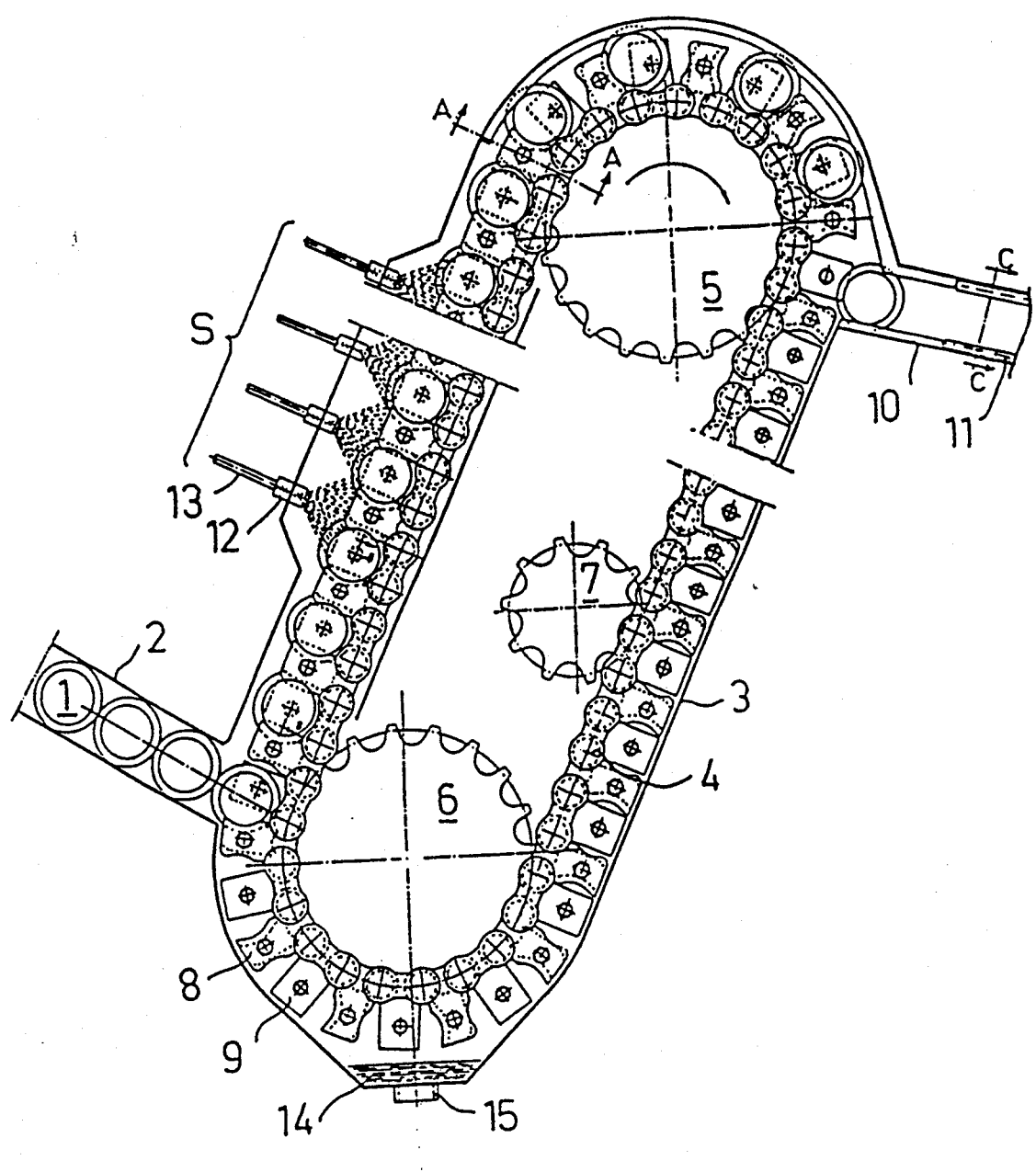
FIG. 1 is a schematic side view of an apparatus in accordance with the present invention.

There is thus illustrated schematically in FIG. 1 a sectional view of the apparatus in accordance with the invention. Through a supply conveyer 2 the stoppers 1 for washing are taken from a plant where they have been oriented and checked and into the closed chamber 3, in which there is situated a washing station S. Inside the closed chamber 3 there is a chain conveyer including a chain 4, an upper chain wheel 5 having an unillustrated shaft passing out through the closed chamber and connected in some way to a drive motor for driving around the chain conveyer inside the closed chamber 3, a lower chain wheel 6 and a chain wheel tensioning sprocket 7. Profiled dogs 8 and support plates 9 are arranged on the links 4 of the chain, such that alternate links carry a profiled dog and the links therebetween carry a support plate 9. The profiled dogs 8 and the support plates 9 are fastened to the links of the chain 4 such that they project outwardly from the chain in relation to the chain wheels 5 and 6.

The supply conveyer 2 is suitably arranged as illustrated in FIG. 1, so that it opens out into the closed chamber 3 approximately opposite the lower chain wheel 6. The profiled dogs 8 and support plates 9 are rigidly attached to the chain 4, and thus when they pass a chain wheel 5 or 6 they will be mutually separated as illustrated in FIG. 1, and always be kept radially directed towards the center of the chain wheel. Where the supply conveyer 2 opens out into the closed chamber 3 the profiled dogs 8 are thus still somewhat separated, and therefore a stopper 1 can roll in between two dogs 8 and have its wider surface supported by a support plate 9. The dogs 8 are profiled so that when they are completely mutually parallel their profiles grip the wider part of each stopper 1. When the chain moves further so that it comes into its straight conveying part, the dogs 1 are mutually parallel, as mentioned, and clamp against the wider part of the stopper 1 for retaining it. With the aid of the chain 4 the stoppers 1 are conveyed upwards from the supply conveyer 2, along the lefthand part of the apparatus as illustrated in FIG. 1, to pass the washing station S. At the upper chain wheel 5 the profiled dogs 8 begin once again to separate and thereby release their grip on the stoppers 1, which were clamped by them during their upward travel. However, the stoppers 1 accompany the dogs around the greater part of the chain wheel, and out to a delivery means 10 situated approximately opposite the upper chain wheel 5. The stoppers 1 fall by gravity into the delivery means 10 and are taken by gravity along a delivery duct 11, which is also closed, and reads the stoppers further to the next station in the line, for example, a packing station or a sterilizer.

The washing station S can be of optional embodiment, but is preferably implemented such as illustrated in the figures, namely with a plurality of jets 12 fastened in the casing to the closed chamber 3, with the jet openings situated inside the chamber and provided with supply lines 13 outside the chamber. It is then most suitably arranged so that the first jets in the conveying direction spray detergent liquid onto the stoppers and the following jets spray a rinsing liquid onto the stoppers. The closed chamber 3 is suitably formed such that at its bottom it includes a collection trough 14 for used washing liquid and has an outlet pipe 15 connected to the trough for taking away the used washing and rinsing liquid.

Figure 2:
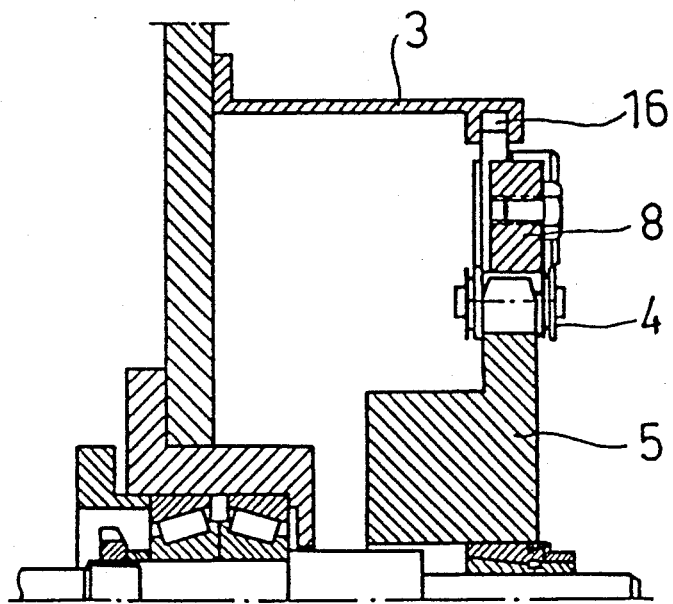
FIG. 2 is a detail section along the line A—A in FIG. 1.

FIG. 2 illustrates a detail along the section A—A in the upper part of FIG. 1. From it will be seen the upper portion of the closed chamber 3, at the free end of which there is arranged a groove 16 for guiding the edge of a stopper 1, which is retained between two dogs 8. In this figure can also be seen the chain 4 and the upper chain wheel 5 with a tooth meshing against the chain 4.

Figure 3:
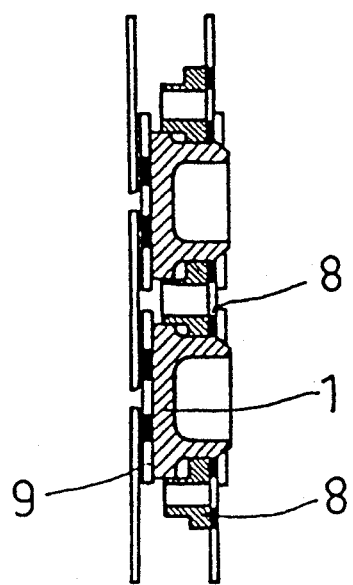
FIG. 3 is a detail section along the line B—B in FIG. 1.

In FIG. 3 there is another detail section along the line B—B in FIG. 1 and showing a section through stoppers and profiled dogs 8 retaining the stoppers 1 along the straight conveying part of the chain. In this Figure it will be seen that the dogs 8 engage against opposing sides of the stoppers 1 and also that the support plates 9 support the flat surface of the larger portion of the stoppers 1.

Figure 4:
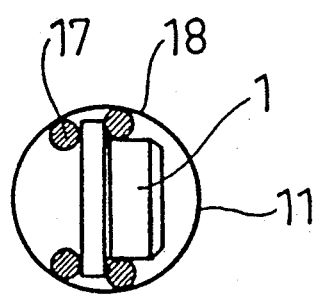
FIG. 4 is a section along the line C—C in FIG 1.

In FIG. 4 there is shown a section through the delivery duct 11, taken along the line C—C in FIG. 1 and showing a stopper 1 situated inside the duct 11. Guides 17 and 18 are also shown, these guides being arranged in the duct 11 for keeping the stoppers 1 reliably oriented in the right attitude so that they are taken to the next station in the correct orientation.

Although not directly shown in the figures, jets can be also arranged at the end of the washing station S for gas drying the stoppers. Alternatively, such jets can be arranged in the delivery duct 11.

As indicated in FIG. 1, the apparatus can have a considerably greater height than is directly apparent from the figure. In this case it is very advantageous that the apparatus is oriented with its extension in height, so as not to require such a large space which otherwise would be required if it had a more horizontal extension. A further advantage with this is that by arranging the supply conveyer 2 at the bottom the advance of the stoppers to the apparatus can be done with the aid of gravity, and by arranging the delivery means 10 at the upper part of the apparatus conveyance to the next work station can also be obtained with the aid of gravity.

I claim:

1. An apparatus for washing position oriented stoppers in a closed environment while retaining the orientation of the stoppers, the apparatus comprising:
   a closed chamber;
   a chain conveyor located in the closed chamber for receiving position oriented stoppers, the chain conveyor including two spaced chain wheels, a chain passing over the chain wheels; and a plurality of dogs fixedly attached to at least some of the chain links, said chain conveyor defining curved portions around said chain wheels and straight portions interconnecting said curved portions;
   supply conveyor communicating with the closed chamber at a location of one of the chain wheels;
   a washing station located along one of the straight portions for washing the stoppers; and
   a closed delivery means in communication with the closed chamber at a location of the other chain wheel and adapted for receiving washed stoppers remaining in the oriented position;
   wherein said dogs are adapted for gripping stoppers, each stopper between two adjacent dogs, and carrying them along the straight portions of the chain conveyer, said dogs being adapted for moving away from each other together with the chain links while passing along the curved portions of said conveyor to allow receiving the stoppers from the supply conveyor in between the dogs, and further adapted for carrying the position oriented stoppers clamped between the dogs along the straight portion past said washing station and for releasing the grip and feeding the stoppers in the retained orientation to the delivery means.

2. An apparatus as claimed in claim 1, wherein one of the chain wheels is arranged substantially higher than the other chain wheel and wherein the supply conveyer communicates with the lower situated chain wheel while the delivery means connects to the upper situated chain wheel.

3. An apparatus as claimed in claim 2, wherein the washing station is situated substantially between the two chain wheels.

4. An apparatus as claimed in claim 3, wherein the washing station includes a plurality of jets for washing and rinsing the stoppers as they are conveyed by the chain conveyor past the washing station.

5. An apparatus as claimed in claim 4, wherein jets for gas drying the stoppers ar arranged after the washing station.

* * * * *